United States Patent [19]

Lasslo et al.

[11] 4,443,450

[45] Apr. 17, 1984

[54] PLATELET AGGREGATION INHIBITORY AGENTS AND INTERMEDIATES THEREFOR

[75] Inventors: Andrew Lasslo, Memphis; Ronald P. Quintana, Germantown; Marion Dugdale; Randy W. Johnson, both of Memphis, all of Tenn.

[73] Assignee: Research Corporation, Tucson, Ariz.

[21] Appl. No.: 368,863

[22] Filed: Apr. 15, 1982

[51] Int. Cl.³ .................. C07D 401/00; A61K 31/495
[52] U.S. Cl. .................................... 424/250; 544/365; 546/189; 546/153; 546/262; 424/258; 424/267
[58] Field of Search .......................... 544/365; 424/250

[56] References Cited

PUBLICATIONS

J. Org. Chem., vol. 22, pp. 837–838, (1957), Lasslo et al.
J. Org. Chem., vol. 21, pp. 958–960, (1956), Lasslo et al.
J. Pharm. Sci., vol. 52, pp. 1186–1188, (1963), Quintana et al.
J. Med. Chem., vol. 7, pp. 698–701, (1964), Beasley et al.
J. Pharm. Sci., vol. 54, pp. 785–787, (1965), Quintana et al.
J. Med. Chem., vol. 10, pp. 1178–1180, (1967), Quintana et al.
J. Med. Chem., vol. 10, pp. 257–259, (1967), Ross.
Adv. Mass. Spectrum, vol. 8A, pp. 828–831, (1980), Mendelbaum et al.
Chem. Abstr., vol. 79, p. 501, abstr. 85665z, (1973), Janssens et al., (to Agfa-Gevaert A.G.): Ger. Offen. 2,254,573.
Chem. Abstr., vol. 59, abstr. 7476b–f (1963), Grudzinski: Lodz, Towarz. Nauk. Wydzial III, Acta, Chim., vol. 8, pp. 105–118, (1962), (in English).
J. Org. Chem., vol. 45, pp. 629–632, (1980), Newkome et al.
Chem. Abstr., vol. 92, p. 653, abstr. 92: 585606, (1980), Bald: Chem. Scr., vol. 13, p. 47, (1979), (in English).
Chem. Abstr., vol. 94, pp. 746–747, abstr. 94: 139627u, (1981), Chugai Pharmaceutical Co., Ltd.: Jpn, Kokai Tokkyo Koho 80 81, 861.
Chem. Abstr., vol. 83, Abstr. 164018b, (1975), Brit. Pat. 1,400,994.

*Primary Examiner*—Donald G. Daus
*Assistant Examiner*—S. A. Gibson
*Attorney, Agent, or Firm*—Scully, Scott, Murphy & Presser

[57] ABSTRACT

Various bis-nitrogen containing compounds exhibiting blood platelet aggregation inhibiting activity. One such compound being [substituted-N, N¹-Bis-(nipecotyl)]-piperazine.

3 Claims, 2 Drawing Figures

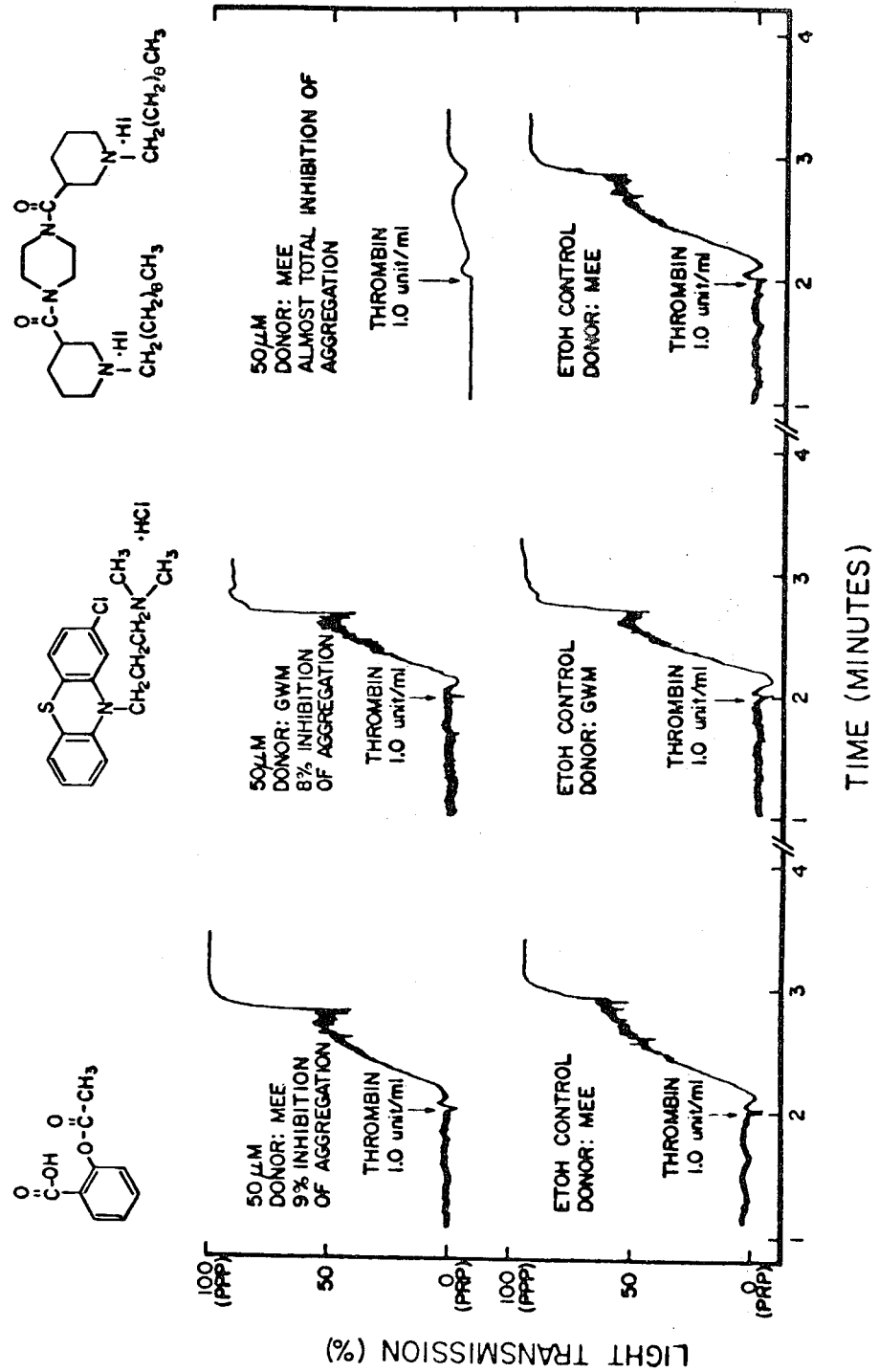

PLATELET AGGREGATION INHIBITORY AGENTS AND INTERMEDIATES THEREFOR

RELATED U.S. APPLICATION DATA

Application Serial No. 347,037, titled PLATELET AGGREGATION INHIBITORY AGENTS and filed on Feb. 8, 1982 in the names of Andrew Lasslo, Ronald P. Quintana and Marion Dugdale, contains subject matter which is related to the invention described and claimed herein. The disclosure of that application is incorporated herein by reference.

BACKGROUND OF THE INVENTION

The present invention relates to certain novel compounds useful as platelet aggregation inhibitory agents and other novel compounds useful as intermediates in the preparation thereof.

Thromboembolic disorders have been shown to be directly related to the susceptibility of blood platelets to adenosine diphosphate (ADP) and thrombin induced platelet aggregation and to other adhesion-release-aggregation chain reactions. Animals wearing prosthetic devices or whose blood is exposed to biomaterials during renal dialysis, blood oxygenation, cardiac catheterization, etc., are especially predisposed to thromboembolic disorders.

The susceptibility of animal blood platelets to aggregation has also been shown to be directly related to the platelet membrane stability.

Certain chemical compounds are known to inhibit platelet aggregation. Thus, aspirin, sulfinpyrazone and dipyridamole are known platelet aggregation inhibiting agents. See Quintana et al, *Thromb. Res.*, Vol 20, pages 405–415 (1980); Cucuianu et al, *J. Lab. Clin. Med.*, Vol. 77, pages 958–974 (1971) and Zucker et al. *J. Lab. Clin. Med.*, Vol. 76, pages 66–75 (1970).

It is an object of the present invention to provide a composition and method for inhibiting blood platelet aggregation thereby being useful for the treatment of thromboembolic disorders.

It is further an object of the present invention to provide a novel class of compounds having platelet aggregation inhibiting activity and platelet membrane stabilization characteristics useful for the treatment of thromboembolic disorders.

SUMMARY OF THE INVENTION

The present invention is predicated on the discovery that compounds of the following structural formulae exhibit blood platelet aggregation inhibiting activity when administered to animals in need thereof:

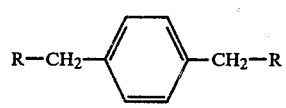  [A]

Wherein R is

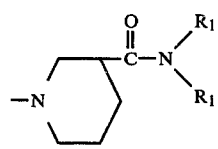

and $R_1$ is alkyl;

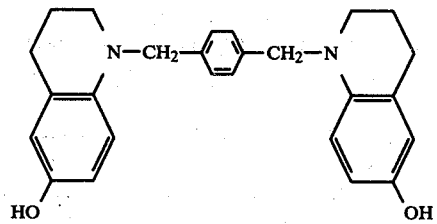  [B]

  [C]

Wherein $R_2$ is

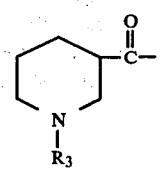

and $R_3$ is alkyl or H;

  (D)

Wherein $R_4$ is

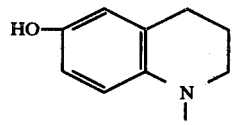

$R_5$ is H or $R_4$,
n=4 or 8 when $R_5$ is H, and
n=8 when $R_5$ is $R_4$;

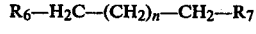  (E)

Wherein $R_6$ is

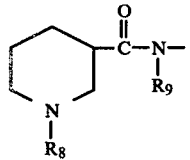

$R_7$ is $R_6$ or H,
$R_8$ is H or alkyl,
$R_9$ is H or lower alkyl, and
n is 0, 2, 4, 6 or 8; and (F) Addition salts thereof with pharmaceutically acceptable acids.

The invention also relates to methods for the inhibition of blood platelet aggregation comprising the administration to an animal in need thereof a blood platelet aggregation inhibitory amount of a compound of the above formulae.

The invention also relates to a pharmaceutical composition in unit dosage form suitable for usage in the above described method comprising a pharmaceutically acceptable carrier and a blood platelet aggregation inhibitory amount of a compound of the above structural formulae.

The compounds are preferably compounded in unit dosage form with pharmaceutically acceptable carriers such as, e.g., (1) tablets: lactose, starch 5%-acacia 2% in water, corn starch, calcium stearate; (ii) capsules: lactose; (iii) parenterals: sterile solid or constituted aqueous solution, including antibacterial, antioxidant, chelating and buffering agents; (iv) suppositories: cocoa butter, and administered orally, parenterally, or rectally to animals in need thereof.

The invention also relates to certain novel compounds having little or no platelet aggregation inhibiting activity but which are useful as intermediates in the preparation of the above-described active compounds.

The intermediate compounds have the structural formulae:

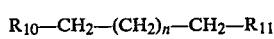  (A)

Wherein
$R_{10}$ is

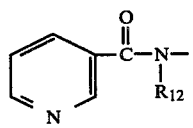

$R_{11}$ is H,
$R_{12}$ is alkyl, and
n is 6;

  (B)
(B)

Wherein
$R_{13}$ is

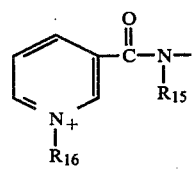

$R_{14}$ is H or $R_{13}$,
$R_{15}$ is alkyl or H,
$R_{16}$ is alkyl, and
n is 4 or 8;

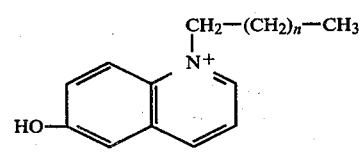  [C]

Wherein n is 4 or 8; and

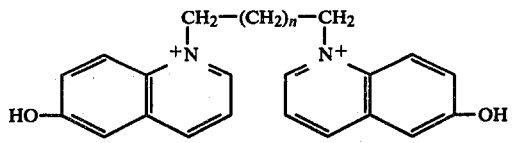

Wherein n is 8;

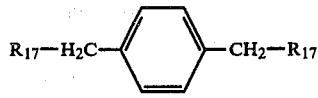  [D]

Wherein
$R_{17}$ is

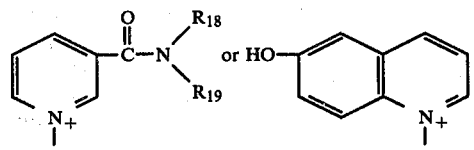

$R_{18}$ is alkyl, and
$R_{19}$ is alkyl;

  [E]

Wherein
$R_{20}$ is

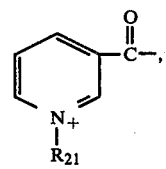

and
$R_{21}$ is alkyl, and
(F) Addition salts thereof with pharmaceutically acceptable acids.

With respect to the term, "alkyl", the preferred groups, in the amide function, are the lower alkyl groups, i.e. alkyl groups having one to six carbon atoms.

DESCRIPTION OF THE DRAWINGS

FIG. 2 depicts inhibition of thrombin-induced human blood platelet aggregation effected by Example 37 in comparison with aspirin and chlorpromazine.

DETAILED DESCRIPTION OF THE INVENTION

Figure 1:
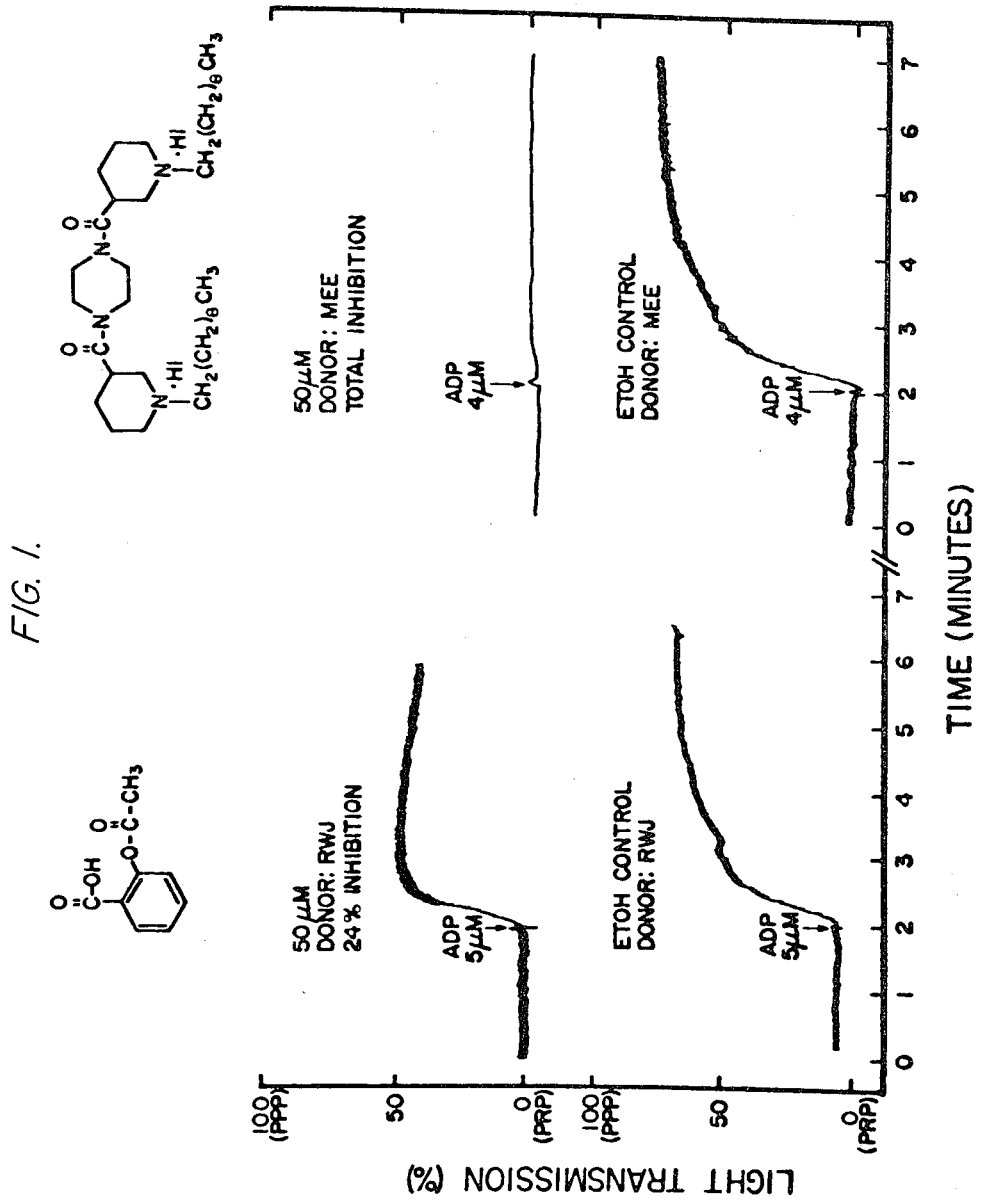
FIG. 1 depicts inhibition of ADP-induced human blood platelet aggregation effected by Example 37 in comparison with aspirin.

The present invention is predicated on the indentification of a particular set of structural features in certain chemical compounds which appear ideal for the constructive penetration of the human blood platelet plasma membrane's lipid bilayer and for effecting membrane stabilization. Quintana et al [*Thromb. Res.*, Vol. 22, pages 665–680 (1981)] conceived of and synthesized certain carbamoylpiperidinoalkanes and -aralkanes incorporating these features, remarkably suited for the penetration to, and subsequent interaction with, negatively charged phospholipids which are prominently instrumental in the platelet aggregation process. Moreover, independently, the cationic form of the penetrated compounds can be envisioned as blocking the mobiliation of $Ca++$ ions by stimuli up to given levels of intensity thereby increasing the threshold effecting $Ca++$-dependent phospholipase $A_2$ and/or phospholipase C activity. It was further substantiated that tertiary amide and tertiary amino groups elicit optimal activity. The tertiary amines in the piperidine moieties have a particularly pivotal function (Quintana, Lasslo and Dugdale, *Biophys. J.*, Vol. 37, pages 130–133 (1982)). Being generally subject to broad variances in protonation they can assume in carefully tailored molecules appropriate hydrophobic character for the penetration of the platelet membrane's lipid bilayer without interfering with the subsequent generation of adequate cationic species (Quintana, Lasslo, Dugdale and Goodin, *Thromb. Res.*, Vol. 22, pages 665–680 (1981)); Quintana Lasslo and Dugdale, *Biophys. J.*, Vol. 37, pages 130–133 (1982)). In addition, the compounds incorporate other molecular components to enhance their lipophilic character, as necessary, for tuning hydrophobic bonding and, thereby, facilitating their action (Quintana, Lasslo and Queen, *Chem.-Biol. Interactions*, Vol. 38, 135–144 (1982)).

In studies of individual phospholipids (Quintana, Lasslo and Greer, *Thromb. Res.*, Vol. 24, pages 379–395 (1981)), involving the matching features and serving as prototypes of actual platelet membrane constituents, the compounds disclosed in the above-identified U.S. patent application Ser. No. 347,033 registered strong interaction with phosphatidylserine (PS) and phosphatidylinositol (PI), none with phosphatidylcholine (PC), and barely interacted with phosphatidylethanolamine (PE). These results are significant since phosphatidylserine and phosphatidylinositol are deemed to constitute the dominant components of platelet factor 3, the catalytic surface for elements of the platelet aggregation process (Caen et al, *Platelets: Physiology and Pathology:* New York, Stratton International, 1977; pages 17–18) (cf. Bode et al, *Ann. N.Y. Acad. Sci.*, Vol. 370, pages 348–358 (1981)). Lewis and Majerus (*J. Clin. Invest.*, Vol. 48, pages 2114–2123 (1969)) and Zwall (*Biochim. Biophys. Acta.*, Vol. 515, pages 163–205 (1978)) have stressed the major role of PS in aggregation, and Gerrard et al (Calcium Mobilization; in *Platelets in Biology and Pathology*-2, J. L. Gordon, ed., New York, Elsevier/North Holland, 1981; page 430) depicts PI in a "loaded gun" arrangement, triggered among the "earliest events" in ADP and thrombin stimulated platelets.

The novel active compounds described herein and methods for their preparation and use are illustrated by the following non-limiting examples:

Representative Procedure A. N,N'-Bis(nicotinoyl)piperazine (Example 34) was prepared by a procedure adapted from the one reported by Badgett et al. (*J. Am. Chem. Soc.*, Vol. 67, pages 1135–1138 (1945)). Thus, thionyl chloride (71.4 g, 0.600 mole) was added dropwise to a cold stirred mixture of 73.9 g (0.600 mole) of nicotinic acid, 94.9 g (1.20 moles) of pyridine and 196 ml of toluene. After the reaction mixture was gradually heated to 90° C. and maintained at this temperature for 1–2 hr, 25.8 g (0.300 mole) of piperazine dissolved in 120 ml of hot toluene was dispensed gradually into the reaction mixture from a dropping funnel in which the solution was maintained hot by circulating steam or hot water through the funnel's jacket. The stirred mixture was maintained at 90° C. for a additional 1–2 hr, after which it was poured into 500 ml of ice water and the pH adjusted to 9.0 with sodium carbonate. The resulting suspension was extracted with a total of 950 mml of chloroform, the chloroform extract dried over anhydrous magnesium sulfate, the drying agent was removed, the filtered solution decolorized by boiling with charcoal and the charcoal removed by filtration through Celite. The filtrate was reduced in volume to 400 ml whereupon crystallization ensued, yielding the product with properties indicated in Table 1. As indicated in the tabulation, Ross (*J. Med. Chem.*, Vol. 10. pages 257–259 (1967)) reported the preparation of this compound by a different procedure without recording the yield. The present method produced 42.2% of analytical grade product.

Representative Procedure $A_1$. Same as Procedure A, except that the amine was added directly to the nicotinic acid-thionyl chloride-pyridine mixture in the absence of toluene.

Representative Procedure B. 1,10-Bis[N-(1-methylnicotinoyl) amino]decane diiodide (Example 27) was prepared employing an adaptation of the procedure described by Lasslo and Kimura (*J. Am. Pharm. Assn., Sci. Ed.*, Vol. 39, pages 43–46 (1950)) (cf. Karrer, Ber., Vol. 49, pages 2057–2079 (1916); Keller and Bernhard, *Arch. Pharm.*, Vol. 263, pages 401–424 (1925); Pyman, *J. Chem. Soc.*, Vol. 113, pages 222–234 (1918)). 1,10-Bis(N-nicotinoylamino)decane (13.0 g, 0.034 mole) was dissolved in 459 ml of 95% ethanol and 292 ml of water, 96.5 g (0.680 mole) of methyl iodide was added, and the mixture was stirred for 5 min. Sodium carbonate (31.5 g, 0.297 mole) was then introduced, and the contents of the reaction vessel were heated at 42°–45° C. for 8 hr. The reation mixture was concentrated, in vacuo, removing excess methyl iodide, ethanol and most of the water. The resulting aqueous slurry was extracted with 250 ml of 95% ethanol. The solvent was removed under vacuum. The crude product (24.4 g, quantitative crude yield) was recrystallized from 95% ethanol, yielding the compound with the physical properties described in Table 1.

Representative Procedure $B_1$. Same as Procedure B except that the compound was extracted from the aqueous slurry with chloroform.

Representative Procedure $B_2$. Same as Procedure B except that the compound was extracted from the aqueous slurry with boiling absolute ethanol, charcoal treated, filtered through Celite and allowed to crystallize from the same.

Representative Procedure $B_3$. Same as Procedure B except that it is conducted without sodium carbonate, and anhydrous benzene was substituted for the aqueous ethanol reaction vehicle (cf. Lasslo. Marine and Waller, *J. Org. Chem.*, Vol. 21, pages 958–960 (1956); Lasslo and Waller, *J. Org. Chem.*, Vol. 22, pages 837–838 (1957).

Representative Procedure $B_4$. Same as Procedure B except that it is conducted without sodium carbonate, and absolute ethanol was substituted for the aqueous ethanol reaction vehicle.

Representative Procedure B$_5$. Same as Procedure B except that it is conducted without sodium carbonate, and ethanol-acetone was substituted for the aqueous ethanol reaction vehicle (cf. Quintana, Smith and Lorenzen, *J. Pharm. Sci.*, Vol. 54, pages 785-787 (1965)).

Representative Procedure B$_6$. Same as Procedure B except that it is conducted without sodium carbonate, and quaternization was effected by heating the amine and alkyl halide reactants, without any solvent, under a nitrogen atmosphere (cf. Few, Gilby, Ottewill and Parreira, *J. Chem. Soc.*, pages 4712-4713 (1958)).

Representative Procedure C. 1,10-Bis[N-(1-methylnipecotoyl)amino]decane dihydriodide (Example 28) was prepared in accordance with the procedure described by Lasslo et al for related compounds (Lasslo, Marine and Waller, *J. Org. Chem.*, Vol. 21, pages 958-960 (1956); Lasslo and Waller, *J. Org. Chem.*, Vol. 22, pages 837-838 (1957)). Thus, 12.0 g (0.018 mole) of 1,10-bis[N-(1-methylnicotinoyl)amino]decane diiodide was dissolved in a mixture of 125 ml of absolute ethanol and 125 ml of water, and subjected to hydrogenation (at maximum pressures of 45-50 psi and at ambient temperature) in the presence of 1.0 g of platinum oxide (Adams' catalyst). When hydrogen uptake ceased, the catalyst was removed by filtration and the solvent by distillation under reduced pressure. Subsequent to drying at 75° C./0.020 mm Hg for 2 hr, the residue constituted the analytical sample (11.8 g, 96.7%) with the properties described in Table 1. In other instances, the products so obtained were purified by recrystallization from appropriate solvents.

Representative Procedure C$_1$. Same as Procedure C except that a specific ratio of ethanol to water was required for solubilization of the unsaturated intermediate. E.g., 4.0 g (0.007 mole) of α,α'-bis(6-hydroxyquinolinium)-p-xylene dibromide (Example 4) was dissolved in 150 ml of boiling water contained in the Parr hydrogenation vessel. Immediately after cessation of heating, 95% ethanol was added to the hot solution increasing the volume to a total of 275 ml. Platinum oxide (0.5 g) was added and the contents of the reaction vessel were maintained at 50° C., employing a Parr heating mantle and thermistor probe, during the entire period of hydrogenation.

Representative Procedure D. 1,2-Bis(N-nipecotoyl-N-methylamino)ethane dihydrobromide (Example 39). In accordance with a procedure described by Lasslo et al (Lasslo, Marine and Waller, *J. Org. Chem.*, Vol. 21, pages 958-960 (1956); Lasslo and Waller, *J. Org. Chem.*, Vol. 22, pages 837-838 (1957)), 10.0 g (0.036 mole) of 1,2-bis(N-nicotinoyl-N-methylamino)ethane (Example 38) was dissolved in 50 ml of water. To the solution was added 12.0 ml of 48% HBr. The solution was filtered through Celite and, upon dilution to a total volume of 275 ml, subjected to hydrogenation (at maximum pressures of 45-50 psi and at ambient temperature) in the presence of 1.0 g of platinum oxide (Adams' catalyst). When hydrogen uptake ceased, the catalyst was removed by filtration and the solvent by distillation under reduced pressure. The residue (16.7 g, quantitative yield) was purified by dissolving in boiling absolute ethanol with activated charcoal. The charoal was removed by filtration through Celite and the white crystalline product obtained, after removal of the solvent by distillation under reduced pressure, was highly hygroscopic.

The physical characteristics and analyses of the examples prepared according to the above procedures (referenced in the Method column) are set forth in Table 1. Some inactive compounds (and their intermediates) are included for comparison with the active entities since the relationships between molecular constitution and platelet aggregation inhibitory potency are important.

TABLE 1

| EXAMPLE | Compound | METHOD of PREPARATION | M.P.°C. or (B.P.°C.) or [n$_D^{25}$] | ANALYSES | | | | | | | | |
|---|---|---|---|---|---|---|---|---|---|---|---|---|
| | | | | C, % | | H, % | | N, % | | Br, % | | I, % |
| | | | | Calcd. | Found | Calcd. | Found | Calcd. | Found | Calcd. | Found | Calcd. | Found |
| 13 | N,N—Dibutylnicotinamide (Intermediate[1]) | A | (129.0–134.0/0.03 mm Hg) | 71.76 | 71.87 | 9.46 | 9.40 | 11.95 | 12.02 | — | — | — | — |
| 23 | 1-Methyl-3-(N,N—dibutylcarbamoyl)piperidine Hydroiodide | B$_1$,C | 98.5–99.0 | 47.12 | 47.09 | 8.17 | 8.16 | 7.33 | 7.40 | — | — | 33.19 | 33.19 |
| 20 | N—Methyl-N—octylnicotinamide (Intermediate) | A$_1$ | (155.0–156.0/0.10 mm Hg) | 72.54 | 72.65 | 9.74 | 9.77 | 11.28 | 11.26 | — | — | — | — |
| 21 | N—Methyl-N—octylnipecotamide | C | (148.0–148.5/0.15 mm Hg) | 70.82 | 70.93 | 11.88 | 12.00 | 11.01 | 11.02 | — | — | — | — |
| 22 | 1-Methyl-3-(N—methyl-N—octylcarbamoyl)piperidine Hydroiodide | B$_1$,C | [1,5305] | 48.49 | 48.35 | 8.39 | 8.28 | 7.07 | 7.03 | — | — | 32.02 | 32.14 |
| 29 | 1,6-Bis(N—nicotinoyl-amino)hexane | A$_1$ | 165.0–166.5 | 66.24 | 66.23 | 6.79 | 6.89 | 17.17 | 17.08 | — | — | — | — |
| 26 | 1,10-Bis(N—nicotinoyl-amino)decane (Intermediate[3]) | A | 168.5–168.9 | 69.08 | 68.82 | 7.90 | 7.80 | 14.65 | 14.45 | — | — | — | — |
| 27 | 1,10-Bis[N—(1-methylnicotinoyl)amino]decane Diiodide | B | 146.0–147.5 | 43.26 | 43.39 | 5.44 | 5.59 | 8.41 | 8.32 | — | — | 38.09 | 38.17 |
| 28 | 1,10-Bis[N—(1-methylnipecotoyl)amino]decane Dihydriodide | C | 98.5–99.5 | 42.49 | 42.30 | 7.13 | 7.20 | 8.26 | 8.05 | — | — | 37.41 | 37.45 |
| 33 | 1,10-Bis(N—methylpiperidinium)decane Diiodide | B$_1$ | 267.0–269.0 | 44.60 | 44.60 | 7.83 | 7.86 | 4.73 | 4.74 | — | — | 42.84 | 42.93 |
| 32 | α,α'-Bis(N—nicotinoyl-amino)-m-xylene (Intermediate) | A$_1$ | 173.0–174.0 | 69.35 | 69.21 | 5.24 | 5.23 | 16.17 | 16.15 | — | — | — | — |
| 19 | α,α'-Bis[3-(N—decylcarbamoyl)piperidino]-p-xylene Dihydrobromide | C$_1$ | 203.0–203.5 | 59.99 | 59.98 | 9.06 | 9.03 | 7.00 | 6.98 | 19.95 | 19.74 | — | — |
| 14 | α,α'-Bis[3-(N,N—dibutylcarbamoyl)piperidino]-p-xylene Dihydrobromide | B$_5$,C | 256.5–257.5 | 58.06 | 58.16 | 8.66 | 8.69 | 7.52 | 7.51 | 21.46 | 21.58 | — | — |
| 34 | N,N'—Bis(nicotinoyl)-piperazine (Intermediate[4]) | A | 201.5–202.5 | 64.85 | 64.75 | 5.44 | 5.57 | 18.91 | 18.91 | — | — | — | — |
| 37 | N,N'—Bis(1-decylnipecotoyl)piperazine Dihydroiodide | C$_1$ | 279.0–280.0 | 51.18 | 50.97 | 8.35 | 8.26 | 6.63 | 6.73 | — | — | 30.04 | 30.16 |
| 10 | 1-Hexyl-6-hydroxyquinolinium Iodide | B$_6$ | 92.5–93.5 | 50.43 | 50.19 | 5.64 | 5.58 | 3.92 | 3.87 | — | — | 35.52 | 35.42 |
| 11 | 1-Hexyl-6-hydroxy-1,2,3,4-tetrahydroquinoline Hydroiodide | C | 152.5–153.5 | 49.87 | 49.96 | 6.70 | 6.73 | 3.88 | 3.87 | — | — | 35.13 | 35.18 |
| 8 | 1-Decyl-6-hydroxyquino- | B$_6$ | 87.0–89.5 | 55.21 | 55.23 | 6.83 | 6.99 | 3.39 | 3.37 | — | — | 30.70 | 30.73 |

TABLE 1-continued

| EXAMPLE | Compound | METHOD of PREPARATION | M.P.°C. or (B.P.°C.) or [nD25] | ANALYSES | | | | | | | | |
|---|---|---|---|---|---|---|---|---|---|---|---|---|
| | | | | C, % | | H, % | | N, % | | Br, % | | I, % | |
| | | | | Calcd. | Found | Calcd. | Found | Calcd. | Found | Calcd. | Found | Calcd. | Found |
| 9 | linium Iodide (Intermediate) 1-Decyl-6-hydroxy-1,2,3,4-tetrahydroquinoline Hydriodide | C | 144.0-145.0 | 54.68 | 54.72 | 7.73 | 7.72 | 3.36 | 3.35 | — | — | 30.41 | 30.61 |
| 12 | 1-Tetradecyl-6-hydroxy-1,2,3,4-tetrahydroquinoline Hydriodide | B₆,C | 148.0-149.0 | 58.35 | 58.30 | 8.51 | 8.67 | 2.96 | 2.93 | — | — | 26.80 | 26.84 |
| 7 | 1,10-Bis(6-hydroxy-1,2,3,4-tetrahydroquinolino)decane Dihydriodide | C₁ | 217.0-218.0 | 48.57 | 48.56 | 6.11 | 6.24 | 4.05 | 3.98 | — | — | 36.65 | 36.59 |
| 4 | α,α'-Bis(6-hydroxyquinolinium)-p-xylene Dibromide | B₅ | 310.0-317.0 (decomposition) | 56.34 | 56.15 | 4.00 | 4.13 | 5.05 | 4.99 | 28.83 | 28.87 | — | — |
| 5 | α,α'-Bis(6-hydroxy-1,2,3,4-tetrahydroquinolino)-p-xylene-Dihydrobromide | C₁ | 287.0-288.5 | 55.53 | 55.42 | 5.38 | 5.51 | 4.98 | 4.85 | 28.42 | 28.27 | — | — |
| 2 | α,α'-Bis(1,2,3,4-tetrahydroisoquinolino)-p-xylene Dihydrobromide⁵ | C₁ | 298.0-299.0 | 58.88 | 58.76 | 5.70 | 5.78 | 5.28 | 5.27 | 30.13 | 29.99 | — | — |
| 36 | N,N—Bis(1-decylnicotinoyl)piperazine Diiodide | B₄ | 250.0-251.5 | 51.93 | 51.82 | 7.02 | 7.02 | 6.73 | 6.67 | — | — | 30.48 | 30.41 |
| 18 | α,α'-Bis[3-(N—decylcarbamoyl)pyridinium]-p-xylene Dibromide (Intermediate) | B₅ | 255.5-256.2 | 60.91 | 60.92 | 7.67 | 7.56 | 7.10 | 7.03 | 20.26 | 20.34 | — | — |
| 1 | α,α'-Bis(isoquinolinium)-p-xylene Dibromide | B₅ | 350.0-352.0 (decomposition) | 59.79 | 59.83 | 4.25 | 4.28 | 5.36 | 5.29 | 30.60 | 30.45 | — | — |
| 16 | α,α'-Bis[3-(N,N—didecylcarbamoyl)piperidino]-p-xylene Dihydrobromide | C | 225.0-227.0 | 66.44 | 66.55 | 10.44 | 10.42 | 5.18 | 5.23 | 14.78 | 14.78 | — | — |
| 43 | 1,6-Bis[N—(1-decylnipecotoyl)-N—butylamino]hexane Dihydriodide | B₄,C | 61.0-62.0 | 55.97 | 55.95 | 9.39 | 9.26 | 5.68 | 5.77 | — | — | 25.71 | 25.73 |
| 42 | 1,6-Bis[N—(1-decylnipecotoyl)-N—methylamino]hexane Dihydriodide | B₄,C | 63.0-64.5 | 53.21 | 52.99 | 8.93 | 8.89 | 6.21 | 6.26 | — | — | 28.11 | 27.95 |
| 3 | α,α'-Bis(quinolinium)-p-xylene Dibromide | B₅ | 360.0° (decomposition) | 59.79 | 59.79 | 4.25 | 4.27 | 5.36 | 5.35 | 30.60 | 30.62 | — | — |
| 17 | N—decylnicotinamide (Intermediate⁷) | A | 71.0-72.0 | — | — | — | — | — | — | — | — | — | — |
| 6 | 1,10-Bis(6-hydroxy- | B₆ | 256.0-256.5 | — | — | — | — | — | — | — | — | — | — |

TABLE 1-continued

| EXAMPLE | Compound | METHOD of PREPARATION | M.P.°C. or (B.P.°C.) or [nD25] | ANALYSES | | | | | | | | |
|---|---|---|---|---|---|---|---|---|---|---|---|---|
| | | | | C, % | | H, % | | N, % | | Br, % | | I, % | |
| | | | | Calcd. | Found | Calcd. | Found | Calcd. | Found | Calcd. | Found | Calcd. | Found |
| 15 | quinolinium)decane Diiodide (Intermediate⁸) | | | | | | | | | | | | |
| | α,α'-Bis[3-(N,N—didecylcarbamoyl)pyridinium]-p-xylene Dibromide | A₁,B₅ | 139.0–140.0 | 67.40 | 67.62 | 9.43 | 9.24 | 5.24 | 5.26 | 14.95 | 14.75 | — | — |
| 30 | 1,6-Bis[N—(1-methylnicotinoyl)amino]hexane Diiodide (Intermediate) | B₂ | 197.0–198.0 | 39.36 | 39.20 | 4.62 | 4.68 | 9.18 | 9.14 | — | — | 41.60 | 41.60 |
| 31 | 1,6-Bis[N—(1-methylnipecotoyl)amino]hexane Dihydriodide | C | 112.0–113.5 | 38.66 | 38.64 | 6.33 | 6.30 | 9.02 | 9.06 | — | — | 40.85 | 40.73 |
| 24 | 1-Methyl-3-(N—decylcarbamoyl)pyridinium Iodide (Intermediate) | B₂ | 119.5–120.5 | 50.50 | 50.55 | 7.23 | 7.25 | 6.93 | 6.90 | — | — | 31.39 | 31.37 |
| 25 | 1-Methyl-3-(N—decylcarbamoyl)piperidine Hydriodide | C | 55.0–56.0 | 49.76 | 49.70 | 8.60 | 8.52 | 6.83 | 6.79 | — | — | 30.92 | 30.78 |
| 35 | N,N—Bis(nipecotoyl)piperazine Dihydrobromide | D | 319.0–319.5 | 40.87 | 40.83 | 6.43 | 6.41 | 11.91 | 11.84 | 33.98 | 33.87 | — | — |
| 38 | 1,2-Bis(N—nicotinoyl-N—methylamino)ethane (Intermediate⁹) | A | 143.8–144.8 | 64.41 | 64.39 | 6.08 | 6.05 | 18.78 | 18.66 | — | — | — | — |
| 39 | 1,2-Bis(N—nipecotoyl-N—methylamino)ethane Dihydrobromide | D | 157.0–158.5 | 40.69 | 40.66 | 6.83 | 6.94 | 11.86 | 11.89 | 33.84 | 33.83 | — | — |
| 40 | 1,2-Bis[N—(1-decylnipecotoyl)-N—methylamino]ethane Dihydrobromide | B₄,C | 98.0–99.0 | 51.06 | 51.18 | 8.57 | 8.62 | 6.61 | 6.83 | 29.97 | 29.91 | — | — |
| 41 | 1,2-Bis[N—(1-hexylnipecotoyl)-N—methylamino]ethane Dihydriodide | B₄,C | 125.0–126.0 | 45.78 | 45.73 | 7.68 | 7.67 | 7.63 | 7.68 | — | — | 34.55 | 34.59 |
| 44 | 1,6-Bis[N—(1-hexylnipecotoyl)-N—butylamino]hexane Dihydriodide | B₄,C | 72.0–73.0 | 52.17 | 52.15 | 8.76 | 8.76 | 6.40 | 6.35 | — | — | 29.01 | 28.73 |

TABLE 1-continued

| EXAMPLE | Compound | METHOD of PREPARATION | M.P. °C. or (B.P.°C.) or [$n_D^{25}$] | ANALYSES | | | | | | | |
|---|---|---|---|---|---|---|---|---|---|---|---|
| | | | | C, % | | H, % | | N, % | | Br, % | I, % |
| | | | | Calcd. Found | | Calcd. Found | | Calcd. Found | | Calcd. Found | Calcd. Found |
| | odide | | | | | | | | | | |

[1] The preparation of this intermediate, using a different procedure, was reported by Bald (Chem. Scr., Vol. 13, page 47 (1979)). No physical properties were cited in the accessible literature.
[2] This intermediate was apparently prepared, using a similar procedure, by the Chugai Tokkyo Koho 80-81,861/1980; Chem. Abstr. Vol. 94, 139627u (1981). No physical properties were cited in the accessible literature.
[3] This intermediate was apparently prepared, using a similar procedure, by the Chugai Pharmaceutical Company (Jpn. Kokai Tokkyo Koho 80-81,861/1980; Chem. Abstr., Vol. 94, 139627u (1981). No physical properties were cited in the accessible literature.
[4] This intermediate has been prepared by Ross (J. Med. Chem., Vol. 10, pages 257–259 (1967)), m.p. 201° C.
[5] Mandelbaum and Bel (Adv. Mass. Spectrom., Vol. 8A, pages 828–831 (1980), reported the synthesis of this compound but did not cite a melting point or other physicochemical characteristics. The compound is inactive, but its bis(6-hydroxy-1,2,3,4-tetrahydroquinoline) analog (Example 5) registered significant effect as an inhibitor of ADP-induced platelet aggregation.
[6] This compound is an intermediate for the tetrahydro-derivative.
[7] Literature, m.p. 72.1–72.4° C. (Badgett, Provost, Ogg and Woodward, J. Am. Chem. Soc., Vol. 67, pages 1135–1138 (1945)).
[8] It was authenticated through its tetrahydro-derivative, compound of Example 7.
[9] This intermediate has been prepared by Newkome and Kawato (J. Org. Chem., Vol. 45, pages 629–632 1980)); m.p. 140.5–141.5° C.

The following samples illustrate the determination of the platelet aggregation inhibiting activity of the compounds of the invention.

Adenosine diphosphate (ADP) used to induce platelet aggregation was employed as the sodium salt. A 10 mM stock solution was prepared fresh before each use in modified Tyrode's buffer and working dilutions were prepared with modified Tyrode's buffer immediately prior to use. The buffer contained NaCl (137.00 mM), KCl (2.70 mM), NaHCO$_3$ (11.90 mM), NaH$_2$PO$_4$.H$_2$O (0.36 mM) and glucose (5.60 mM) in redistilled water. Adjustment to pH 7.4 was effected by addition of 1N HCl. A solution of highly purified human α-thrombin (10,624 units/ml) was stored at $-70°$ C. in 10 μl aliquots. The latter were diluted with modified Tyrode's buffer to a concentration of 10.0 units/ml immediately prior to use.

Venous blood for the examples set forth below was collected in plastic syringes from healthy male volunteers (aged 21–30 years) who had fasted overnight and had abstained from all medications, alcohol, tobacco and caffeine for a period of at least one week prior to donations. In experiments employing ADP as the aggregation-inducing agent, the blood was transferred into siliconized centrifuge tubes containing 3.2% sodium citrate (blood/citrate ratio 8:1); in thrombin-induced aggregations, 3.8% sodium citrate (blood/citrate ratio 9:1) was used. The citrated whole blood was centrifuged at 120×g for 15 minutes at 23° C., yielding platelet-rich plasma (PRP); platelet-poor plasma (PPP) was obtained by centrifugation of citrated whole blood at 1,100×g for minutes at 23° C. The platelet count of PRP was determined and adjusted to a final count of 300,000 platelets per mm$^3$ by dilution with autologous PPP. (Occasionally, blood from a given donor yielded PRP with a count lower than the stipulated figure; however, this was usually greater than 285,000, and never less than 250,000 platelets per mm$^3$.) The plasma so obtained was transferred in 1.2-ml aliquots to siliconized glass tubes, by means of a siliconized Pasteur pipet. In order to maintain plasma pH in the appropriate range, the air in the tubes was displaced gently (1 minute) with a 5% CO$_2$-95% air (v/v) mixture and the tubes sealed with Parafilm according to the method of Han et al, *Br. J. Haematol.* Vol. 26, pages 373–389 (1974). The plasma was maintained at 37° C. in a water bath until used in the aggregation experiments.

Assays of platelet aggregation were performed at least in duplicate, using plasma acquired from different donors, employing a method developed by Quintana et al (Quintana et al, *Thromb. Res.*, Vol. 22, pages 665–680 (1981); Quintana et al, *Thromb. Res.*, Vol. 20, pages 405–415 (1980) (cf. Born, *Nature,* Vol. 194, pages 927–929 (1962) and Mustard et al, *J. Lab. Clin. Med.*, Vol. 64, pages 548–559 (1964)).

Initially, in each experiment, 0.45-ml aliquots of PRP were placed in siliconized cuvettes and stirred (1,100 rpm) in the aggregometer at 37° C. to ascertain the absence of spontaneous aggregation. Appropriate ADP solutions (50 μl) were subsequently injected using a Hamilton microliter syringe to determine the minimal concentration eliciting maximal biphasic aggregation. This ranged from 2 μM to 8 μM (cf. Quintana et al, *Thromb. Res.*, Vol. 22, pages 665–680 (1981); Quintana et al, *Thromb. Res.*, Vol. 20, pages 405–415 (1980)). In each case, the concentration of ADP so determined was used in eliciting aggregation throughout each specific set of aggregometric evaluations. In all thrombin-induced aggregation experiments the same stimulus was applied; this constituted injection of 50 μl; of the solution containing 10.0 units of α-thrombin/ml (affording a final concentration of 1.0 unit of α-thrombin/ml PRP).

0.5 μl of a solution of the evaluant compound in redistilled 95% ethanol was injected into a stirred (1,100 rmp) 0.45-ml aliquot of plasma in a siliconized cuvette in the aggregometer-well (37° C.). After 15 seconds, the cuvette was transferred to an incubator (also at 37° C.) and the contents held at this temperature, without stirring, until 2 minutes post-injection. The cuvette was then returned to the aggregometer well, a base-line being recorded for 2 minutes to detect any spontaneous aggregation. At exactly 4 minutes after injection of the evaluant solution, 50 μl of the appropriate ADP or thrombin solution was injected and aggregation recorded. Evaluants were studied, normally, at one or more of the following final concentrations: 500 μM, 100 μM, 50 μM, and 10 μM. Control experiments (e.g., ethanol in a final concentration of 0.095% v/v) were performed in parallel with those involving the respective evaluants, and were initiated either 1 minute prior to or 1 minute after the start of experiments employing the test compounds. This permitted injections to be made precisely at the specified times. Normally, 2 pairs of aggregations were carried out (at 70/71 and 80/81 minutes post-venipuncture). Evaluant and control aggregations were studied in alternate ($Y_1$ or $Y_2$) channels of the dual-channel aggregometer in order to detect any effects due to malfunction of a specific channel.

The pH of a sample of the plasma employed in aggregometric studies was routinely measured at 37° C. after the injection of aggregation-stimulus at 70/71 minutes post-venipuncture. Also, the pH of a second plasma sample, maintained at 37° C. under 5% CO$_2$-95% air mixture, was determined at the conclusion of the 80/81 minute aggregation-pair (e.g., 90 minutes from venipuncture). The readings ranged from 7.5-7.7 in both instances. Plasma pH was not affected perceptibly by the addition of representative evaluants in concentrations employed in this investigation.

In evaluating aggregometric tracings, primary attention was paid to intensity of aggregation, i.e., the maximum change in percentage of light transmittance with special attention to any abolition or diminution of the secondary and even the primary aggregation-waves. Platelet aggregation inhibitory potency was expressed as the % reduction in maximal aggregation intensity effected by the evaluant compound, with respect to the maximal aggregation intensity evident in the corresponding control experiment. In ADP-induced aggregation experiments, as previously observed, the secondary aggregation wave was normally abolished by inhibitory responses of approximately 30% or higher; effects on the primary aggregation wave were evident, normally, in inhibitions of 40% or stronger. (Cf. Roper et al, *Am. J. Clin. Pathol.*, Vol. 71, pages 263–268 (1979)); Mills et al, *Life Sci.*, Vol. 14, pages 659–672 (1974); Newhouse and Clark, in Triplett (Ed.), *Platelet Function: Laboratory Evaluation and Clinical Application,* Chicago, American Society of Clinical Pathologists, 1978, pages 109–121.)

Relationships between the molecular constitution of the evaluant-compounds and their inhibitory effects on platelet aggregation (Cf. Quintana et al, *Thromb. Res.,* Vol. 22, pages 665–680 (1981); Quintana et al, *Thromb. Res.*, Vol. 24, pages 379–395 (1981); Quintana et al, *Chem-Biol. Interactions,* Vol. 38, pages 135–144 (1982);

Quintana et al, Biophys., J., Vol. 37, pages 130–133 (1982) are summarized in Table 2. Under conditions substantially comparable to those reported in Thromb. Res., Vol. 22, pages 665–680 (1981), the compounds of the invention are capable of inhibiting thrombin-induced aggregation without eliminating thrombin-effected clotting.

TABLE 2

Relationships Between Chemical Constitution and Inhibition of Human Blood Platelet Aggregation

| | | % INHIBITION OF AGGREGATION BY INDICATED CONCENTRATIONS OF EVALUANT COMPOUNDS | |
|---|---|---|---|
| EXAMPLE | COMPOUND | ADP-INDUCED AGGREGATION | THROMBIN-INDUCED AGGREGATION |
| 2 | α,α'-Bis(1,2,3,4-tetrahydroisoquinolino)-p-xylene Dihydrobromide | 0% at 50 μM | * |
| 5 | α,α'-Bis(6-hydroxy-1,2,3,4-tetrahydroquinolino)-p-xylene Dihydrobromide | 21.5% at 50 μM | * |
| 7 | 1,10-Bis(6-hydroxy-1,2,3,4-tetrahydroquinolino)decane Dihydriodide | 25.9% at 50 μM | * |
| 9 | 1-Decyl-6-hydroxy-1,2,3,4-tetrahydroquinolino)decane Hydriodide | 33.0% at 50 μM | * |
| 11 | 1-Hexyl-6-hydroxy-1,2,3,4-tetrahydroquinoline Hydriodide | 45.9% at 100 μM<br>37.2% at 50 μM | * |
| 12 | 1-Tetradecyl-6-hydroxy-1,2,3,4-tetrahydroquinoline Hydriodide | 0% at 50 μM | * |
| 13 | N,N—Dibutylnicotinamide (Intermediate) | 0% at 100 μM | * |
| 14 | α,α'-Bis[3-(N,N—dibutylcarbamoyl)piperidino]-p-xylene Dihydrobromide | 49.7% at 50 μM | * |
| 16 | α,α'-Bis[3-(N,N—didecylcarbamoyl)piperidino]-p-xylene Dihydrobromide | 0% at 50 μM | * |
| 19 | α,α'-Bis[3-(N—decylcarbamoyl)piperidino]-p-xylene Dihydrobromide | 0% at 50 μM | * |
| 20 | N—Methyl-N—octylnicotinamide (Intermediate) | 12.1% at 100 μM | * |
| 21 | N—Methyl-N—octylnipecotamide | 49.9% at 100 μM | * |
| 22 | 1-Methyl-3-(N—methyl-N—octylcarbamoyl)piperidine Hydriodide | 33.1% at 100 μM | * |
| 23 | 1-Methyl-3-(N,N—dibutylcarbamoyl)piperidine Hydriodide | 11.8% at 100 μM | * |
| 25 | 1-Methyl-3-(N—decylcarbamoyl)piperidine Hydriodide | 45.6% at 100 μM | * |
| 28 | 1,10-Bis[N—(1-methylnipecotoyl)-amino]decane Dihydriodide | 30.9% at 50 μM | * |
| 31 | 1,6-Bis[N—(1-methylnipecotoyl)amino]hexane Dihydriodide | 17.0% at 500 μM | * |
| 33 | 1,10-Bis(N—methylpiperidinium)-decane Diiodide | 0% at 100 μM | * |
| 35 | N,N'—Bis(nipecotoyl)piperazine Dihydrobromide | 48.9% at 500 μM | * |
| 37 | N,N'—Bis(1-decylnipecotoyl)-piperazine Dihydriodide | 93.8% at 50 μM<br>48.3% at 10 μM | 88.2% at 50 μM |
| 39 | 1,2-Bis(N—nipecotoyl-N—methylamino)ethane Dihydrobromide | 46.3% at 500 μM | * |
| 40 | 1,2-Bis[N—(1-decylnipecotoyl)-N—methylamino]ethane Dihydriodide | 82.6% at 50 μM | * |
| 41 | 1,2-Bis[N—(1-hexylnipecotoyl)-N—methylamino]ethane Dihydriodide | 71.6% at 50 μM | * |
| 42 | 1,6-Bis[N—(1-decylnipecotoyl)-N—methylamino]hexane Dihydriodide | 85.6% at 50 μM | 88.3% at 50 μM |
| 43 | 1,6-Bis[N—(1-decylnipecotoyl)-N—butylamino]hexane Dihydriodide | 38.6% at 50 μM | * |
| 44 | 1,6-Bis[N—(1-hexylnipecotoyl)-N—butylamino]hexane | 72.4% at 50 μM | * |

TABLE 2-continued
Relationships Between Chemical Constitution
and Inhibition of Human
Blood Platelet Aggregation

| | | % INHIBITION OF AGGREGATION BY INDICATED CONCENTRATIONS OF EVALU- ANT COMPOUNDS | |
|---|---|---|---|
| EXAMPLE | COMPOUND | ADP-INDUCED AGGREGATION | THROMBIN-INDUCED AGGREGATION |
| | Dihydriodide | | |

*Not determined.

It would appear that the compounds of the invention are highly effective by penetrating the lipid bilayer of the platelet membrane and by interacting as cations with negatively charged phospholipids (e.g., phosphatidylserine and phosphatidylinositol) within the bilayer's inner segment. It would further appear that, in the event of such penetration, the cationic form of the compounds interferes with phospholipase activation by counteracting stimulus-induced mobilization of Ca++ ions and Ca++-dependent phospholipase activity. It would also appear that activity is dependent upon (i) intramolecular distances between and charge levels of pivotal atoms and/or functions, (ii) molecular geometry and flexibility, and (iii) hydrophobic characteristics of molecular segments.

The data reflect that the compounds possess appropriate hydrophobic character to penetrate the lipid bilayer of the platelet plasma membrane and, subsequently, are capable of generating sufficient quantities of their cationic species to counteract massively stimulus-induced mobilizaton of Ca++ ions and, thereby, restrain or void Ca++-dependent phospholipase activity. By means of this mechanism and their interaction with negatively charged phospholipids (e.g., phosphatidylserine and phosphatidylinositol) within the bilayer's inner segment, the compounds function as effective membrane stabilizing agents. There is corroborating evidence in the literature in support of these contentions. Vanderhoek and Feinstein (Vanderhoek et al, *Mol. Pharmacol.*, Vol. 16, pages 171–180 (1979)) present especially convincing data and cite those of others [Sun et al, *Lipids*, Vol. 14, pages 229–235 (1979): Rittenhouse-Simmons, *J. Clin. Invest.*, Vol. 63, pages 580–587 (1979)] in emphasizing the prominent function of Ca++ in controlling phospholipase-A$_2$ and phospholipase-C activity. The importance of hydrophobic character, in imparting appropriate affinity for molecules to consumate interaction leading to the prevention of Ca++ mobilization, was stressed by Lullman et al [Lullman et al, *Biochem. Pharmacol.*, Vol. 20, pages 2969–2974 (1980)].

The compounds described hereinabove useful for the inhibition of blood platelet aggregation could be administered orally, parenterally, or rectally.

Employing computed plasma concentrations for aspirin, dipyridamole and sulfinpyrazone, the most frequently used antithrombotic agents in contemporary practice, the most potent of the compounds of the invention are effective at lower levels, with due consideration for variances (i) in the extent and rate of absorption, (ii) in biodistribution and protein binding, and (iii) in the rate and diversity of biotransformation. Example 37, in Table 1, inhibits 93.8% ADP-induced and 88.2% thrombin-elicited human blood platelet aggregation. In comparison, at the same concentrations, aspirin effects 24% inhibition in ADP- and 9% inhibition in thrombin-induced aggregation (see FIGS. 1 and 2). The literature suggests an even lesser potency than aspirin for dipyridamole (10% at 250 $\mu$M concentration in ADP-induced aggregation; Cucuiani et al, *J. Lab. Clin. Med.*, Vol. 77, pages 958–974 (1971) and sulfinpyrazone (0% at 2,470 $\mu$M concentrations in ADP-induced aggregation; Packham et al, *J. Exp. Med.*, Vol. 126, pages 171–188 (1967)). Dipyridamole and sulfinpyrazone could exert their effects according to different mechanisms, however. It should be added that chlorpromazine, employed as one of the key reference compounds in exploratory work on platelets, is much less effective in thrombin-induced aggregation than the piperidine derivatives discussed above. It is, also, considerably less effective in ADP-induced aggregation. (See FIG. 2).

The structure of the compounds of this invention would suggest a lower toxicity than those currently in use. Even aspirin's adverse effects are severe enough to counsel against its use by survivors of myocardial infarction (NHLBI-AMISRG, *J. Am. Med. Assoc.*, Vol. 243, pages 661–669 (1980). Indeed, the compounds of this invention would appear to yield less toxic metabolites in the process of their biotransformation. In that respect, piperidine is known to be a natural metabolite and comparatively high quantities have been reported to occur in man (excretion in urine about 3 to 20 mg/day) (Williams, *Detoxication Mechanisms*, 2nd Edition, New York, John Wiley and Sons, 1959, pages 567). Piperidine-3-carboxylic acid (nipecotic acid) has not been discerned to have deleterious effects (Johnston, *Ann. Rev. Pharmacol. Toxicol.*, Vol. 18, pages 269–289 (1978); cf. Krogsgaard-Larsen and Johnston, *J. Neurochem.*, Vol. 25, pages 797–802 (1975)). Nicotinic acid (niacin), its aromatic analog, along with nicotinic acid amide (niacinamide), are known metabolites. Aminoalkanes or aralkanes which could be generated from some compounds of the invention are generally not known to be converted into harmful products (Williams, *Detoxication Mechanisms*, 2nd Edition, New York, John Wiley and Sons, 1959, pages 128–139 and 146–147).

In broader terms of preventive medicine, it may be preferable to inhibit and adhesion-release-aggregation chain reaction at its very inception with platelet membrane stabilizing agents by precluding activities of phospholipases. This is especially true if it is considered that platelet cyclo-oxygenase inhibitors like aspirin incapacitate the patient's platelets for the rest of their life span (Walder et al, *Mol. Pharmacol.*, Vol. 13, pages 407–414 (1977)) and could possibly result in the concurrent inhibition of endothelial cyclo-oxygenase which would reduce or block generation of the endogenous aggregation inhibitor prostacyclin (PGI$_2$) (Moncada et al, in Gilman et al (Eds.), *The Pharmacological Basis of Therapeutics*, 6th Edition, New York, MacMillan, 1980, page 669; cf. Harris et al, *Ann. Rev. Physiol.*, Vol. 41, pages 653–668 (1979)).

Within the context of these considerations, the compounds of the invention could be formulated with suitable pharmaceutically acceptable carriers into a unit dosage form containing from about 28 to about 286 milligrams of active ingredient. Accordingly, orally administered dosages in the range of from about 0.38 to about 3.8 mg/kg of body weight per adult animal, every six hours, would be sufficient to inhibit blood platelet aggregation. For infant or young animals, dosages in the range of from about 0.08 to about 0.76 mg/kg would be sufficient. Obviously, parenteral administration should reduce the referenced quantities, and rectal administration could also require a modification in the dosage.

We claim:

1. A compound having the structural formula:

Wherein $R_2$ is

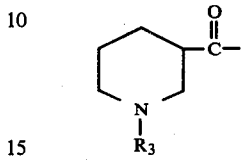

and $R_3$ is alkyl or H.

2. A pharmaceutical composition in unit dosage form suitable for administration to an animal in need thereof comprising a pharmaceutically acceptable carrier and a blood platelet aggregation inhibiting amount of a compound of claim 1.

3. A method for the inhibition of blood platelet aggregation comprising administering to an animal in need thereof a blood platelet aggregation inhibiting amount of a compound of claim 1.

* * * * *

UNITED STATES PATENT AND TRADEMARK OFFICE
CERTIFICATE OF CORRECTION

PATENT NO. : 4,443,450
DATED : April 17, 1984
INVENTOR(S) : Andrew Lasslo, et al.

It is certified that error appears in the above-identified patent and that said Letters Patent are hereby corrected as shown below:

ON THE COVER PAGE:

[73] Assignee: "Research Corporation, Tucson, Ariz." should read as --Research Corporation, New York, New York--.

Column 4, line 27, in the formula, "R~" should read as --$R_{18}$--.

Signed and Sealed this

Twelfth Day of March 1985

[SEAL]

Attest:

DONALD J. QUIGG

Attesting Officer    Acting Commissioner of Patents and Trademarks